(12) United States Patent
Berg et al.

(10) Patent No.: US 11,020,268 B2
(45) Date of Patent: Jun. 1, 2021

(54) MOUTH COOLER

(71) Applicant: BrainCool AB, Lund (SE)

(72) Inventors: Jon Berg, Dalby (SE); Martin Waleij, Lund (SE); Mats Jontell, Borås (SE)

(73) Assignee: BrainCool AB, Lund (SE)

( * ) Notice: Subject to any disclaimer, the term of this patent is extended or adjusted under 35 U.S.C. 154(b) by 500 days.

(21) Appl. No.: 15/503,200

(22) PCT Filed: Aug. 11, 2015

(86) PCT No.: PCT/EP2015/068498
§ 371 (c)(1),
(2) Date: Feb. 10, 2017

(87) PCT Pub. No.: WO2016/023920
PCT Pub. Date: Feb. 18, 2016

(65) Prior Publication Data
US 2017/0231815 A1    Aug. 17, 2017

(30) Foreign Application Priority Data

Aug. 11, 2014 (SE) .................................. 1450930-1

(51) Int. Cl.
| | | |
|---|---|---|
| *A61F 7/12* | (2006.01) | |
| *A61C 19/06* | (2006.01) | |
| *A61M 19/00* | (2006.01) | |
| *A61F 7/00* | (2006.01) | |
| A61M 16/04 | (2006.01) | |

(52) U.S. Cl.
CPC ................ *A61F 7/12* (2013.01); *A61C 19/06* (2013.01); *A61F 7/0085* (2013.01); *A61M 19/00* (2013.01); *A61F 2007/0017* (2013.01); *A61F 2007/0056* (2013.01); *A61F 2007/0063* (2013.01); *A61M 16/049* (2014.02); *A61M 2205/366* (2013.01); *A61M 2205/3606* (2013.01); *A61M 2210/0625* (2013.01)

(58) Field of Classification Search
CPC ...... A61F 2007/0017; A61F 2007/0015; A61F 2007/0056; A61F 7/12; A61F 7/0085; A61F 2007/0063; A61C 19/06; A61C 19/063; A61C 9/06; A61C 9/08; A61M 2210/0625; A61M 2210/0631; A61M 2210/0643; A61M 19/00; A61M 16/049; A61M 2205/3606; A61M 2205/366; A61J 17/02

See application file for complete search history.

(56) References Cited

U.S. PATENT DOCUMENTS

| | | | |
|---|---|---|---|
| 39,673 A | 8/1863 | Oudry | |
| 2,036,735 A * | 4/1936 | Welker ................ | A61C 9/0006 433/35 |

(Continued)

FOREIGN PATENT DOCUMENTS

| | | |
|---|---|---|
| DE | 10162485 A1 | 7/2003 |
| WO | 03011362 A2 | 2/2003 |

*Primary Examiner* — Eun Hwa Kim
*Assistant Examiner* — Adam Z Minchella
(74) *Attorney, Agent, or Firm* — Capitol City TechLaw (57) ABSTRACT

A mouth cooler is provided. The mouth cooler comprises a first peripheral cooling winding shaped and dimensioned to cool the lower and upper jaw, and at least one second cooling winding in arrangement with the peripheral cooling winding shaped and dimensioned to cool at least the blood entry to the tongue.

7 Claims, 6 Drawing Sheets

(56) References Cited

U.S. PATENT DOCUMENTS

| | | | |
|---|---|---|---|
| 2,257,329 A | | 9/1941 | Britt |
| 2,672,143 A | | 3/1954 | Gold et al. |
| 3,439,681 A | | 4/1969 | Riley |
| 3,467,104 A | | 9/1969 | Burbridge et al. |
| 3,878,610 A | * | 4/1975 | Coscina ............... A61C 9/0006 433/37 |
| 4,173,219 A | * | 11/1979 | Lentine ................ A61C 19/063 128/861 |
| 4,983,122 A | | 1/1991 | Mitnick |
| 5,494,441 A | * | 2/1996 | Nicholson .......... A61C 17/0211 433/215 |
| 5,509,801 A | | 4/1996 | Nicholson |
| 5,868,138 A | * | 2/1999 | Halstrom ................ A61F 5/566 128/848 |
| 6,217,606 B1 | * | 4/2001 | Portnoy .................... A61F 7/12 607/108 |
| 2004/0111138 A1 | * | 6/2004 | Bleam ...................... A61F 7/12 607/105 |
| 2009/0216303 A1 | * | 8/2009 | VanSkiver ............. A61C 19/08 607/96 |
| 2010/0108078 A1 | * | 5/2010 | Morgan ............... A63B 71/085 128/861 |
| 2012/0216820 A1 | * | 8/2012 | Scarberry ............. B29C 39/003 128/848 |
| 2014/0230829 A1 | * | 8/2014 | Rogers ................... A61F 5/566 128/848 |
| 2015/0080992 A1 | * | 3/2015 | Drnek ...................... A61F 7/12 607/105 |

\* cited by examiner

MOUTH COOLER

This application claims priority under 35 USC 119(a)-(d) to SE patent application No. 1450930-1, which was filed on Aug. 11, 2014, the entire content of which is incorporated herein by reference.

FIELD OF THE INVENTION

This invention pertains in general to the field of treatment of oral mucositis and/or oral stomatitis. More specifically, the present invention refers to a mouth cooling device, comprising at least one channel system, having an inlet and an outlet for a cooling fluid.

BACKGROUND OF THE INVENTION

Cancer patients undergoing chemotherapy treatments often experience oral mucositis and/or oral stomatitis. The terms oral mucositis and oral stomatitis are often used interchangeably at the clinical level, but they do not reflect identical processes. Oral Mucositis describes inflammation of oral mucosa resulting from chemotherapeutic agents or ionizing radiation, and typically manifests as erythema or ulcerations. Oral stomatitis refers to any inflammatory condition of oral tissue, including mucosa, dentition/periapices, and periodontium, and includes infections of oral tissues as well as mucositis.

Risk of oral mucositis has historically been characterized by treatment-based and patient-based variables. The current model of oral mucositis involves a complex trajectory of molecular, cellular, and tissue-based changes. There is increasing evidence of genetic governance of this injury, characterized in part by upregulation of nuclear factor kappa beta and inflammatory cytokines (e.g., tumor necrosis factor-alpha) and interleukin-1 in addition to epithelial basal cell injury.

Erythematous oral mucositis typically appears 7 to 10 days after initiation of high-dose cancer therapy. High-dose chemotherapy, such as that used in the treatment of leukemia and hematopoietic stem cell transplant regimens, may produce severe mucositis.

It is known that cooling of the oral cavity leads to prevention chemotherapy absorption in the oral cavity; hence leading to reduction and prevention of oral mucositis.

In today's treatment and prevention of oral mucositis, patients undergoing chemotherapy simultaneously have ice cubes in their mouth, which ice cubes are moved around in the mouth by the action of the patient. This is not only messy, but also makes it very difficult to achieve a good cooling of the oral cavity. The sizes of ice cubes are often such that they to not easily reach the warmest parts (the most narrow) of the oral cavity. Also, the water quality from which ice cubes are made can be of poor quality, leading to health hazards as such.

Therefore, it has been proposed to cool oral cavity for the treatment and reduction of oral mucositis through the use of a mouth cooling device with a closed channel system in which a cooling medium is circulated. One such device is disclosed in U.S. Pat. No. 5,509,801. The oral device is formed to be insertable within a patient's mouth and receive a circulated cooling medium to cool the patient's oral tissues including the gums cheeks, tongue, roof and base of the mouth, to reduce the absorption of chemotherapy agent. However, this device has a low cooling efficiency due to poor tissue coverage—especially tissue with a high heat emission. Additionally, this device is uncomfortable and has low cooling efficiency since it is rather bulky and implies static tongue position.

SUMMARY OF THE INVENTION

Accordingly, the present invention preferably seeks to mitigate, alleviate or eliminate one or more of the above-identified deficiencies in the art and disadvantages singly or in any combination and solves at least the above mentioned problems by providing a mouth cooler comprising a first peripheral cooling winding shaped and dimensioned to cool the lower and upper jaw, and at least one second cooling winding in arrangement with the peripheral cooling winding shaped and dimensioned to cool at least the blood entry to the tongue.

Other embodiments of the present invention will be apparent from the enclosed claims.

BRIEF DESCRIPTION OF THE DRAWINGS

These and other aspects, features and advantages of which the invention is capable of will be apparent and elucidated from the following description of embodiments of the present invention, reference being made to the accompanying drawings, in which.

DESCRIPTION OF EMBODIMENTS

The following description focuses on an embodiment of the present invention applicable to a mouth cooler and in particular to a mouth cooler for treatment and prevention of oral mucositis and/or oral stomatitis.

Figure 1:
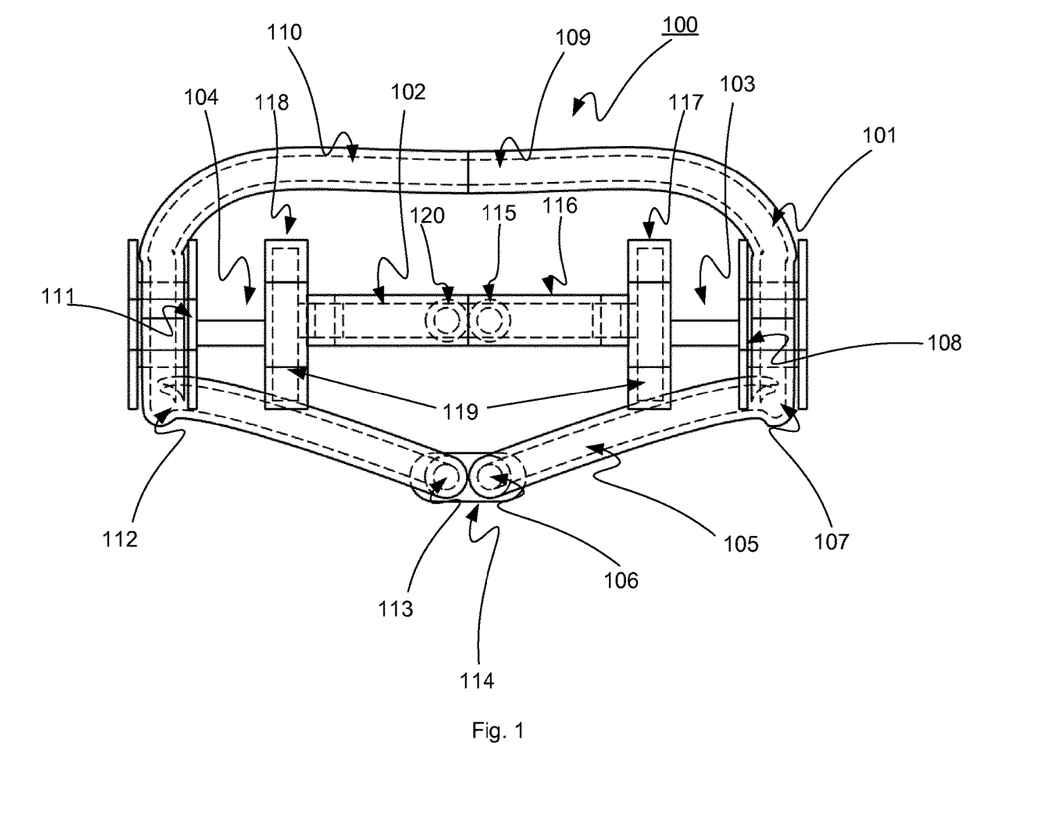
FIG. 1 is a perspective view of the mouth cooling device.
Figure 2:
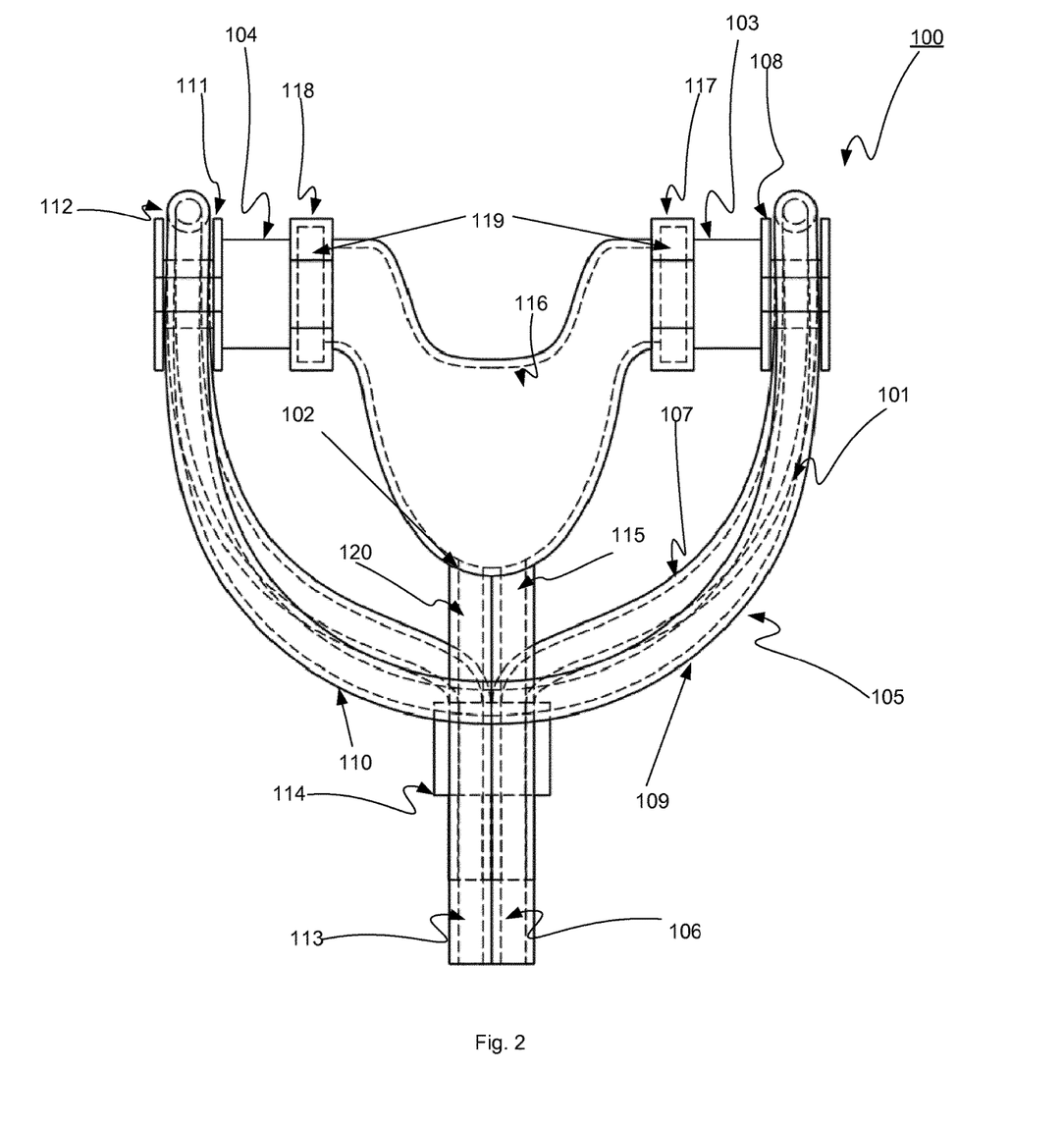
FIG. 2 is a top-down view of the mouth cooling device.

In an embodiment of the invention according to FIGS. 1 and 2, a mouth cooler 100 is disclosed. The mouth cooler 100 comprises two cooling windings, in form of a peripheral cooling winding 101 and a central cooling winding 102. The peripheral cooling winding 101 is shaped and dimensioned to cool the lower and upper jaw, and more specifically the vestibules under the inferior and superior lip. The central cooling winding 102 is shaped and dimensioned to cool the upper side of the tongue alternatively the lower side of the tongue and the floor of the mouth. The mouth cooler also comprises a left and a right bite bridge 103, 104.

The peripheral cooling winding 101 comprises a tubing 105 with a first inlet 106, and down streams said inlet 106 a left inferior part 107. The left inferior part 107 is configured to follow the left part of the vestibule under the inferior lip. The tubing 105 then continues by rounding the left bite bridge 103. The rounding of the left bite bridge 103 is performed via following the contour of a left bite bridge flange 108 of the left bite bridge 103. The left bite bridge flange 108 thus ensures that the tubing 105 not is occluded through biting, when the cooling device 100 is held in place by biting the bite bridges 103, 104. After rounding the left bite bridge flange 108 the tubing 105 continues into a left superior part 109, configured to follow the vestibule under the superior lip.

After passing the superior labial frenulum, the tubing 105 continues into a right superior part 110. The right superior part 110 continues to a right bite bridge flange 111 of the right bite bridge 104, and rounds the right bite bridge 104 via following the contour of the right bite bridge 104 into a right inferior part 112. The right inferior part 112 is configured to follow the vestibule under the inferior lip until it reaches the inferior labial frenulum, where the tubing 105 ends in a first outlet 113. In this way a cooling medium, such as a cooling liquid, such as water, may be circulated from the first inlet 106 to the first outlet 113 along the inferior and superior vestibules of a patient, to effectively cool tissue and blood. Also, the peripheral cooling winding 101 adds in positioning of the cooling device in the mouth of the patient, since the peripheral cooling winding is spatially held in three dimensions along the vestibules. This means, that the sizes of the bite bridges 103, 104 may be kept small, improving patient comfort.

At the first inlet 106 and the first outlet 113, the tubing 105 is provided with a connector 114. The connector 114 is displaceable along the tubing 105 entering and exiting the mouth of the patient. By pushing/pulling the connector 114 along the tubing 105, the size of the peripheral cooling winding 101 may be adapted after the mouth of the patient. When the connector is pushed towards the mouth of the patient the size of the cooling device 100 is decreased and when the connector 114 is pulled away from the mouth of the patient the size of the cooling device 100 is increased.

The central cooling winding 102 has a second inlet 115. The second inlet 115 is configured to lead a cooling medium, such as a cooling liquid, such as water, to a tongue bridge 116. In the tongue bridge 116, the cooling medium, such as a cooling liquid, such as water, is spread over the tongue bridge. Hence, the tongue bridge 116 has inner channels or cavities leading from the second inlet 115 to left and right, such that the cooling medium is divided into two flows of the same magnitude to a right bite bridge flange 117 on the left bite bridge 103, and a left bite bridge flange 118 on the right bite bridge 104. The tongue bridge 116 is configured such that the patient may choose if the tongue bridge should be positioned underneath the tongue to cool the under side of the tongue and the mouth floor, or if the tongue bridge 116 should be positioned on top of the tongue to cool the upper side of the tongue and optionally the palate.

The cooling medium is then distributed in the right bite bridge flange 117 and the left bite bridge flange 118 in cooling cavities 119 therein. In this way, cooling liquid and thus cooling effect reaches the right bite bridge flange 117 and the left bite bridge flange 118 in a homogenous way and synchronous way, with same cooling medium dwell time upon reaching the left and right bite bridges 103, 104. In this way, the cooling effect may be the same at the left and right bite bridges 103, 104. This is preferable, since the right bite bridge flange 117 and the left bite bridge flange 118 are located adjacent the blood entry to the tongue, i.e. the lingual arteries. Hence, the blood may be cooled upon entry into the tongue, whereby the blood itself may act as transporter of cooling effect. The cooling medium is then led from the cooling cavities 119 to the tongue bridge 116 for additional cooling of the tongue, whereafter the cooling medium is led out of the cooling device through a second outlet 120.

A method for cooling the mouth includes flowing a cooling medium through a peripheral cooling winding to arranged at the superior and inferior lip. Cooling medium flowed through this peripheral winding acts to cool the upper and lower jaw. Cooling medium can also be flowed through a central cooling winding arranged to be positioned either above the tongue or between the tongue and the floor of the mouth. Cooling medium flowed through the central cooling winding acts to cool either the tongue and palette or the tongue and floor of the mouth.

Figure 3A:
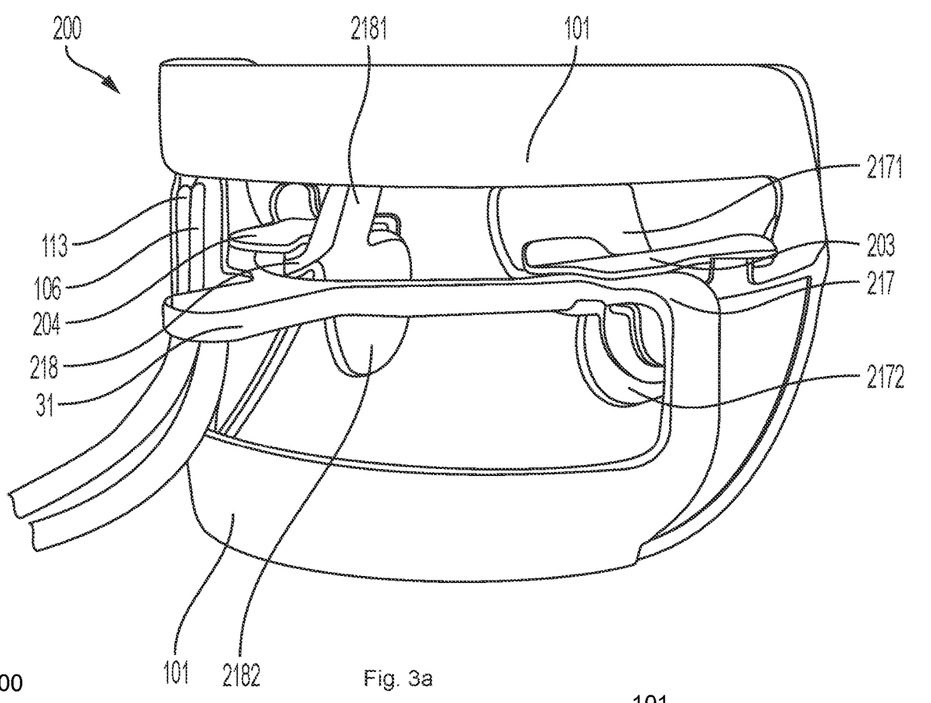
FIGS. 3*a* to 3*c* show an alternative mouth cooling device in different views.
Figure 3B:
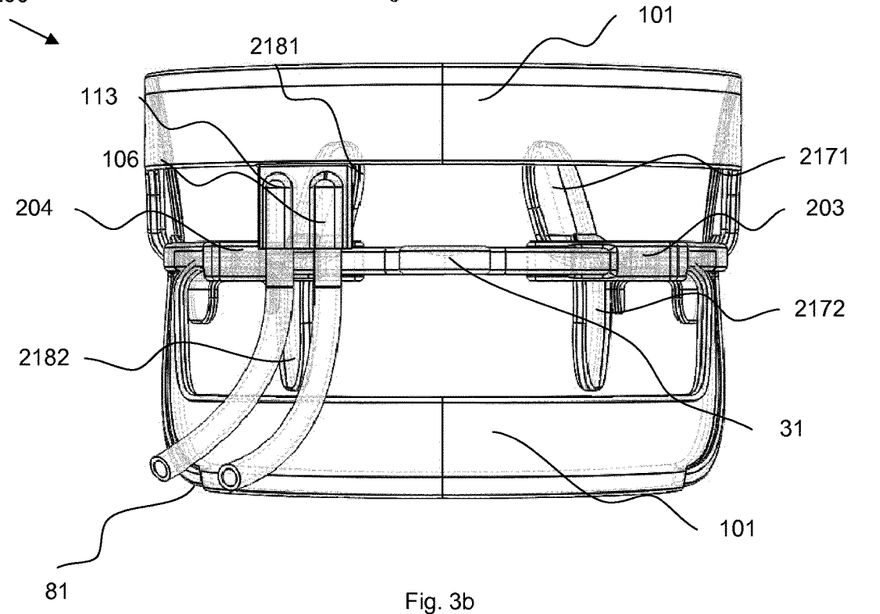
Figure 3C:
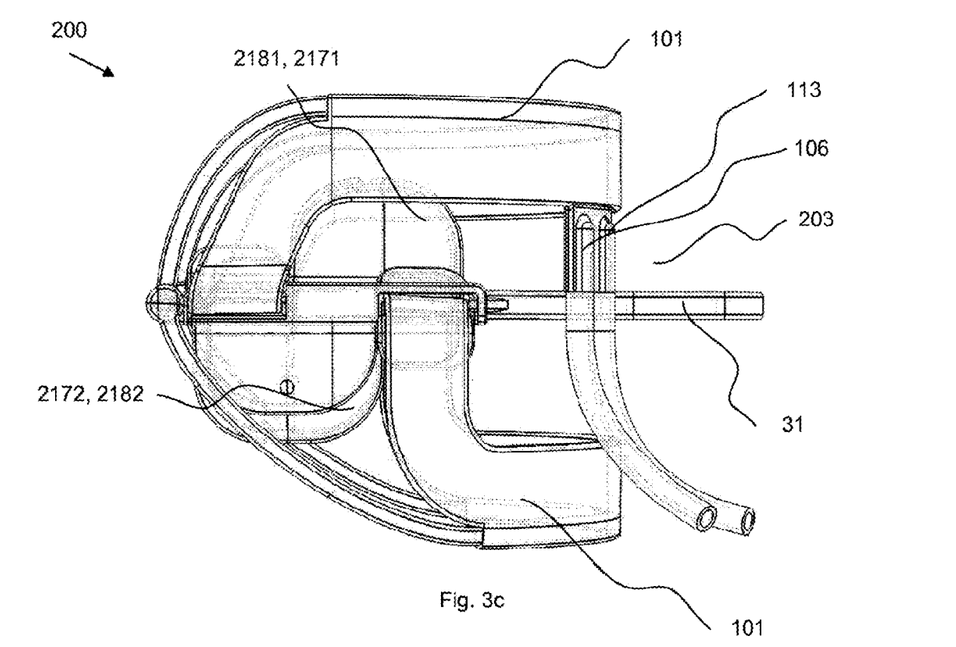

Attention is now drawn to FIGS. 3a to 3c, which shows an alternative mouth cooler 200. In contrast to the mouth cooler explained in view of FIGS. 1 and 2, this mouth cooler 200 does not comprise a central winding 102 or tongue bridge 116. Similarly, to the mouth cooler 100 of FIGS. 1 and 2, the mouth cooler 200 comprises a first peripheral cooling winding 101 shaped and dimensioned to cool the lower and upper jaw. Moreover, at least one second cooling winding 217, 218 is provided in arrangement with the peripheral cooling winding 101 shaped and dimensioned to cool at least the blood entry to the tongue.

As shown in FIGS. 3a to 3c two second windings 217, 218 are shown. Each winding is in fluid connection to the peripheral cooling winding 101. Each second cooling winding 217, 218 is arranged in a bite bridge 203, 204. Each second cooling winding 217, 218 comprises at least two flexible cooling flaps 2171, 2172, 2181, 2182. One of the flexible cooling flaps (see 2171 and 2181 in FIG. 3a) extends above the corresponding bite bridge 203, 204 such as to cool an upper area of the tongue and adjacent palette. The other flexible cooling flap of each second winding extends below (see 2172, 2182 of FIG. 3a) the bite bridge 203, 204 to cool an upper area of the tongue and palette in use. Both flexible cooling flaps are also provided such as to cool the lateral sides of the tongue, i.e. adjacent the blood entry to the tongue, such as the lingual arteries.

The mouth cooler 200 further comprises an inlet 106 for receiving a cooling fluid and an outlet 113 allowing the cooling fluid to exit the mouth cooler. The inlet 106, and/or outlet 113 may be provided in a connector connecting the inlet and/or outlet to the tubing 105 forming the cooling path of the mouth cooler and also to external tubings connected to the cooling fluid etc. In contrast to the mouth cooler of FIGS. 1 and 2, the mouth cooler 200 as shown in FIGS. 3a to 3c only comprise one inlet and one outlet. Hence, the second windings 217, 218 as well as the peripheral winding 101 are provided with cooling fluid from the same inlet 106.

The inlet 106 and/or outlet 113 may be arranged closer to one of the second windings than the other, i.e. adjacent to the labial commisure of the mouth. This may be preferred in terms of improved comfort for the patient. This also means that any obstruction in front of the patient's mouth is kept to a minimum.

Figure 4:
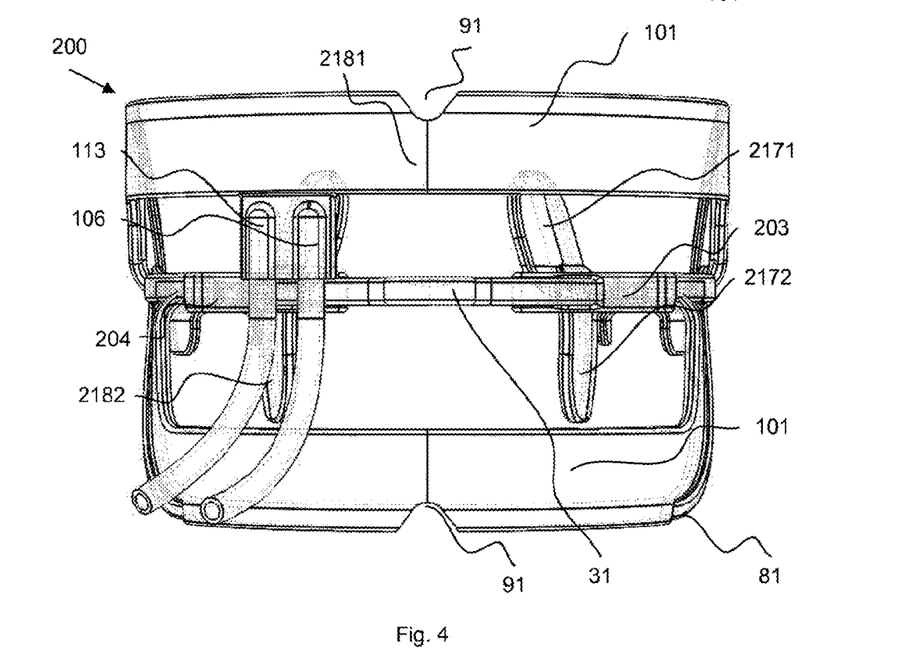
FIG. 4 show mouth cooling device being provided with recesses in the peripheral winding for alleviating pressure on the inferior and superior labial frenulum.

FIG. 4 shows mouth cooling device 200 being similar to that of FIGS. 3a to 3c, but being provided with recesses 91 in the peripheral winding 101 for alleviating pressure on the inferior and superior labial frenulum. This feature increases the comfort and is particularly advantageous for extended treatment times.

Figure 5:
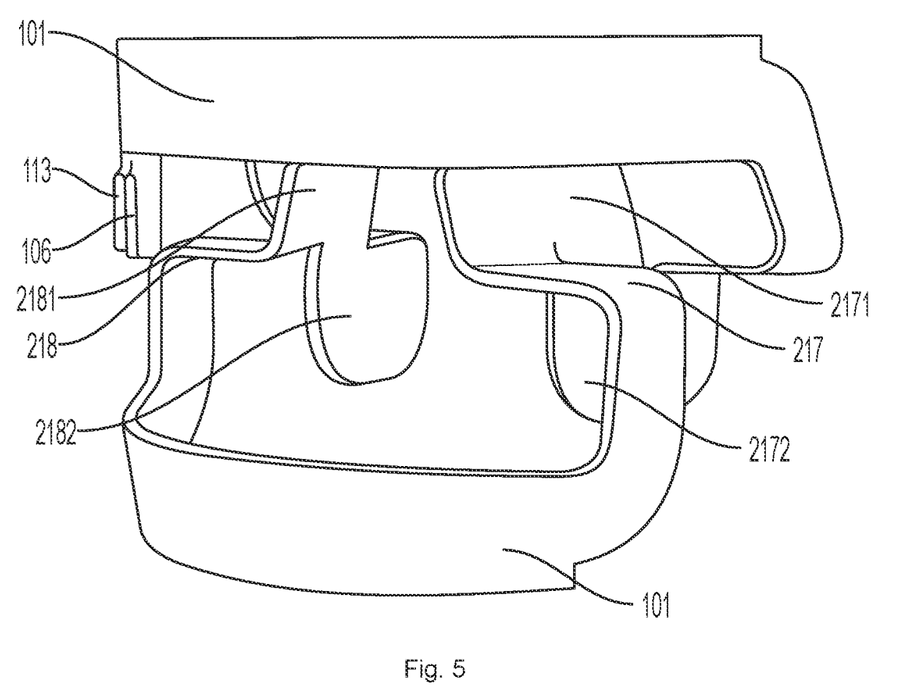
FIG. 5 is a schematic view of the cooling path formed by the tubing of the mouth cooler of FIGS. 3*a* to 3*c* and 4.

FIG. 5 is a schematic view of the cooling path formed by the tubing 105 of the mouth cooler of FIGS. 3a to 3c and 4. The peripheral cooling winding 101 comprises a tubing 105 (not shown in FIG. 5 since integrally provided) extending along the vestibule under the superior lip and through one of the second windings 217. After the second winding 217 it continues along the vestibule under the lower lip and further through the further second winding 218. The tubing comprises an inlet 106 for receiving a cooling fluid and an outlet 113 for allowing the cooling fluid to exit the tubing 105.

Figure 6:
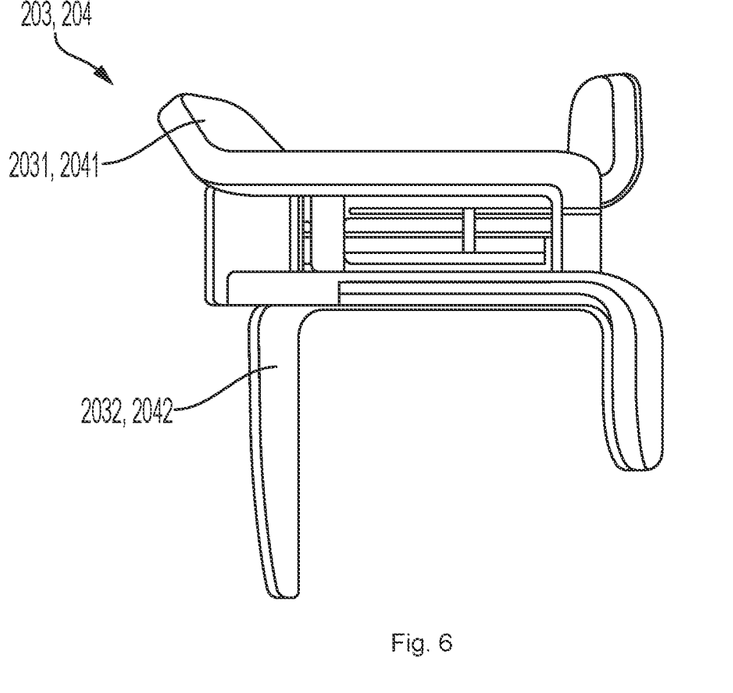
FIG. 6 is a schematic view of a bite bridge of the mouth cooler of FIGS. 3 to 5.

FIG. 6 is a schematic view of a bite bridge 203, 204 of the mouth cooler of FIGS. 3 to 5. From FIG. 6 it is shown that the bite bridge form at least one cavity between the upper and lower bite surfaces in which the second winding is arranged. With reference to FIGS. 5 and 3*a* it should be appreciated that each bite bridge 203, 204 may comprise two cavities. In this way the ends of the second winding connected to the inferior and superior part of the cooling path of the mouth cooler may enter each cavity from the side of the bite bridge facing the corner of the mouth as shown in FIG. 3*a*.

As shown in FIG. 6 each bite bridge 203, 204 may comprise a support flange 2031, 2032, 2041, 2042 for supporting each cooling flap 2171, 2172, 2181, 2182 in use. Other support flanges, as shown on the right side of the bite bridge of FIG. 6, may also be provided to support the second cooling winding entering through the cavity from the side of the bite bridge facing the corner of the mouth as shown in FIG. 3*a*.

Figure 7:
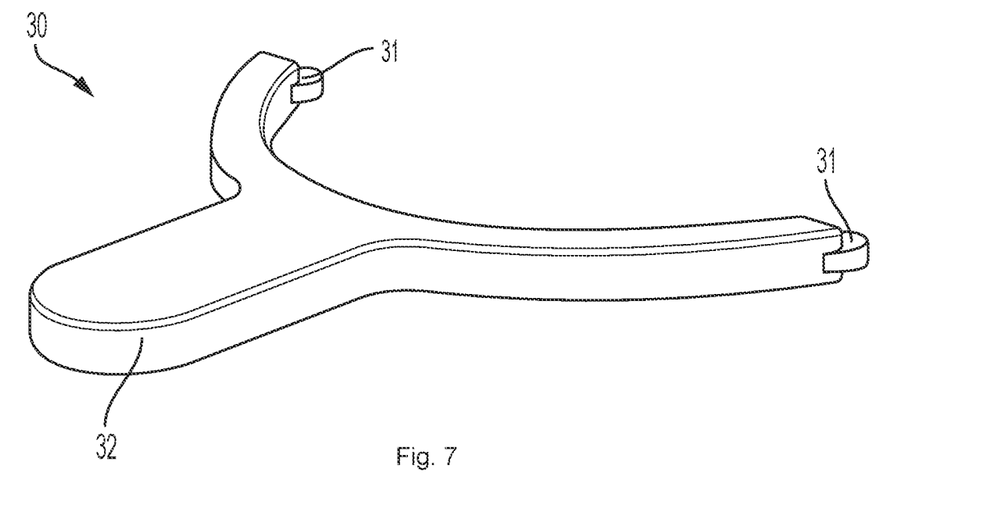
FIGS. 7 and 8 show two alternative detachable mounting members of the mouth cooler.
Figure 8:
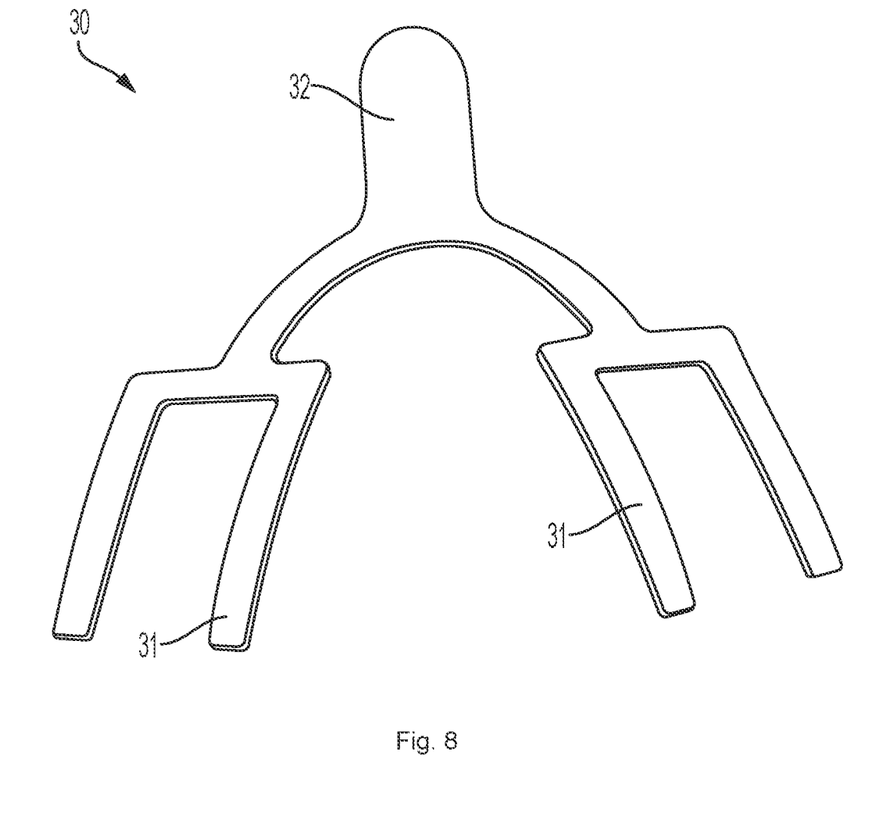

In order to facilitate mounting of the mouth cooler 200 a detachable mounting support member 30, such as that shown in FIG. 7 or 8, may be used. The mounting support member 30 may be detachably connected to each bite bridge 203, 204 for facilitated mounting of the mouth cooler into the mouth of the patient. After the mouth cooler 200 is satisfactory mounted, the mounting support member 30 may be detached from each bite bridge and is removed. Two alternative embodiments of the mounting support member 30 are shown in FIGS. 7 and 8. Both mounting support members comprise two connection members 31 for connection to respective bite bridges, as well as a surface 32 acting as a grip surface for the user mounting the mouth cooler 200. The connection member 31 of FIG. 7 is arranged as a protrusion for connection to a corresponding slot in the bite bridge. In contrast, the connection members 31 of FIG. 8 are provided as forks for clamping around the sides of the corresponding bite bridge in use. It should be appreciated that alternative ways of connecting the mounting support member to the bite bridges are also possible, without departing from the scope of the present invention.

The mouth cooling device can be manufactured from one or more materials. Ideally the material is a non-toxic polymer suitable for use inside the mouth such as silicone.

A method for cooling the mouth includes flowing a cooling medium through a peripheral cooling winding to arranged at the superior and inferior lip. Cooling medium flowed through this peripheral winding acts to cool the upper and lower jaw. Cooling medium can also be flowed from the peripheral winding to two second windings cooling the upper and lower lateral sides of the tongue. The peripheral winding and the second windings are in fluid communication with each other.

In the claims, the term "comprises/comprising" does not exclude the presence of other elements or steps. Furthermore, although individually listed, a plurality of means, elements or method steps may be implemented by e.g. a single unit or processor. Additionally, although individual features may be included in different claims, these may possibly advantageously be combined, and the inclusion in different claims does not imply that a combination of features is not feasible and/or advantageous. In addition, singular references do not exclude a plurality. The terms "a", "an", "first", "second" etc do not preclude a plurality. Reference signs in the claims are provided merely as a clarifying example and shall not be construed as limiting the scope of the claims in any way.

The invention claimed is:

1. A mouth cooler comprising:
   a peripheral cooling winding shaped and dimensioned to cool a lower jaw and an upper jaw; and
   at least one second cooling winding in arrangement with the peripheral cooling winding shaped and dimensioned to cool at least a blood entry to a tongue;
   wherein each of the at least one second cooling winding is in fluid connection to the peripheral cooling winding;
   wherein the peripheral cooling winding includes a tubing configured to extend along a vestibule under an inferior lip and through one of the second cooling windings, and the tubing is configured to extend along a vestibule under a superior lip and through a further second cooling winding, such that the tubing defines a flow path to direct a cooling fluid sequentially through the one second cooling winding, through a portion of the peripheral cooling winding, and through the further second cooling winding;
   wherein the tubing comprises an inlet for receiving the cooling fluid and an outlet for allowing the cooling fluid to exit the tubing; and
   wherein the mouth cooler does not include a tongue bridge shaped to extend across the tongue.

2. The mouth cooler according to claim 1, wherein the peripheral cooling winding is shaped and dimensioned to cool the vestibules under the inferior lip and the superior lip.

3. The mouth cooler according to claim 1, wherein each of the at least one second cooling windings is arranged in a bite bridge.

4. The mouth cooler according to claim 3, wherein each of the at least one second cooling windings comprises at least two flexible cooling flaps, at least one of which is extending above the corresponding bite bridge and configured to cool an upper area of the tongue and palate, and at least one of which extending below the corresponding bite bridge and configured to cool a lower area of the tongue and palate in use.

5. The mouth cooler according to claim 3, further comprising a mounting support member detachably connected to each bite bridge for facilitated mounting of the mouth cooler into a mouth of a patient;
   wherein upon completion of the mounting of the mouth cooler the mounting support member is detached from the mouth cooler in use.

6. The mouth cooler according to claim 4, wherein each bite bridge comprises a support flange for supporting each cooling flap in use.

7. The mouth cooler according to claim 1, wherein at least one of the inlet and the outlet is arranged closer to one of the second cooling windings than the other.

* * * * *